Figure 1:
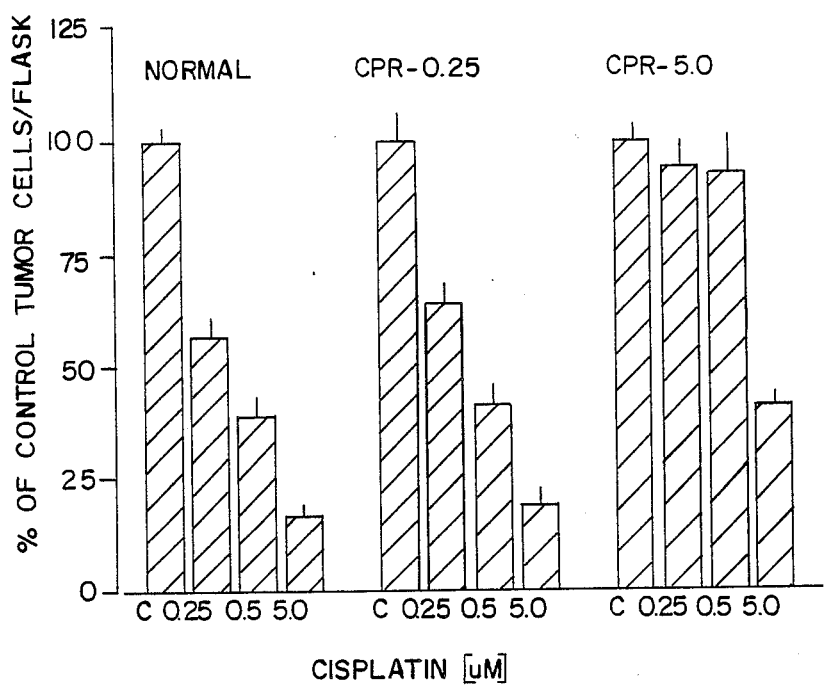

United States Patent [19]

Honn et al.

[11] Patent Number: 4,906,646

[45] Date of Patent: Mar. 6, 1990

[54] METHOD AND COMPOSITION FOR THE TREATMENT OF TUMORS BY ADMINISTERING A PLATINUM COORDINATION COMPOUND AND A CALCIUM CHANNEL BLOCKER COMPOUND OF THE DIHYDROPYRIDINE CLASS

[75] Inventors: Kenneth V. Honn, Grosse Pointe Woods; John D. Taylor, Detroit; James M. Onoda, Royal Oak, all of Mich.

[73] Assignee: Board of Governors of Wayne State University, Detroit, Mich.

[21] Appl. No.: 786,321

[22] Filed: Oct. 10, 1985

Related U.S. Application Data

[63] Continuation-in-part of Ser. No. 480,704, Mar. 31, 1983, Pat. No. 4,690,935.

[51] Int. Cl.$^4$ .......................... C07H 3/02; C07C 31/22
[52] U.S. Cl. .................................................... 514/356
[58] Field of Search ......................................... 514/356

[56] References Cited

U.S. PATENT DOCUMENTS

4,140,707  2/1979  Cleare et al. ..................... 260/420
4,177,263 12/1979  Rosenberg et al. ................ 424/131
4,419,351 12/1983  Rosenberg et al. ................ 424/245

FOREIGN PATENT DOCUMENTS

96299  12/1983  European Pat. Off. .
123850 11/1984  European Pat. Off. .
3008661 9/1980  Fed. Rep. of Germany .

OTHER PUBLICATIONS

Rosenberg, et al., Nature 205:698, (1965).
Rosenberg, et al., Nature 222:385, (1969).
Einhorn et al., Int. Med. 87:293, (1977).
Merrin, C. E., Cancer Treat. Rep. 63:1579, (1979).
Lee et al., Cancer Treat. Rev. 10:39, (1983).
Stoter et al., Cancer 54:1521, 1984.
Belinson, et al, Cancer 54:1983, 1984.
Wittes, et al., Cancer Treat. Rep 63:1533, 1979.
DeVita, V. T., Cancer 51:1209, 1983.
Sutherland, R. M., et al., J. Nat. Cancer Inst. 46:113, 1971.
West, G. W., et al., Cancer Res. 40: 3665, 1980.
Shackney, S. E., et al, Ann Int. Med. 89:107, 1978.
Goldie and Coldman, Cancer Res. 44:3643, 1984.
Fidler, I. J., Cancer Res. 38:2651, 1978.
Tanigawa, N., et al., Cancer Res. 44:2309, 1984.
Bakka, A., et al., Toxicol. Applied Pharmacol. 61:215, 1981.
Giavazzi, R., et al., Cancer Res. 43:2216, 1983.
Yanovich, S., et al., Cancer Res. 44: 1743, 1984.
Benz, C., et al., Cancer Res. 42:2081, 1982.
Ozols, R. F., et al., Cancer Res. 42:4265, 1982.
Ling, V., et al., Cancer Treat. Rep. 67:869, 1983.
Citrin, D. L., et al., Cancer 50:201, 1982.
Inaba, M., et al., Cancer Res. 39:2200, 1979.
Valeriote, F., et al., Cancer Res. 39:2041, 1979.
Tsuruo et al., Cancer Res. 41:1967, (1981); 42:4730, (1982); 43:2267, (1983c); 44:4303, (1984).
Slater, et al., J. Clin. Invest. 70:1131, 1982.
Ganapathi, et al., Cancer Res. 44:5056, 1984.
Murray et al., Cancer Chemotherap. Pharmacol. 13:69, 1984.
Roberts, J. J., In: Molecular Actions and Targets for Cancer Chemotherap. Agents, Academic Press, N.Y. p. 17, 1981.
Curt et al., Cancer Treat. Rep 68:87, 1984.
Sigdestad et al., Cancer Treat. Rep. 65:845, 1981.
Rose et al., Cancer Treat. Rep. 66:135, 1982.

(List continued on next page.)

Primary Examiner—Paul J. Killos
Attorney, Agent, or Firm—Ian C. McLeod

[57] ABSTRACT

A method for the treatment of malignant tumors by co-administering a platinum coordination compound and a dihydropyridine class calcium channel blocker compound is described. The compounds are administered over a period of several days in at least two separate dosages of each compound so as to produce regression of the tumor in vitro and in vivo and inhibition of metastasis of the tumor in vivo.

19 Claims, 8 Drawing Sheets

OTHER PUBLICATIONS

Clement et al., Cancer Res. 40:4165, 1980.
Mizuno and Ishida, Biochem. Biophys. Res. Commun. 107:1021, 1982.
Tsuruo et al., Cancer Res. 43:808, (1983a); 43:2905, (1983b).
Rogan et al., Science 224:994, (1984).
Akazawa, S., et al., Kagaku Nyoko 11:943-7 (1984).
Kessel and Wilberding, Biochem. Pharmacol. 33:1157, 1984.
Sloane, et al., Science, 212, 1151-1153 (1981).
Honn, K. V., et al., Proc. Soc. Expl. Biol. Med. 174:16, 1983.
Onoda, J. M., et al., Thromb. Res. 34:367, 1984.
Flaim and Zlis, Fed. Proc. 40:2881, 1981.
Bernard, P. P., et at., Cancer Treat. Rep. 67:457, 1983.
Robins, A. B., et al., Cancer Treat. Rep. 67:245, 1983.
Guarino, A. M., et al., Cancer Res. 39:2204, 1979.
Kaelin, W. G., et al., Cancer Res. 42:3944, 1982.
Chafouleas, J. G., et al., Science 224:1346, 1984.

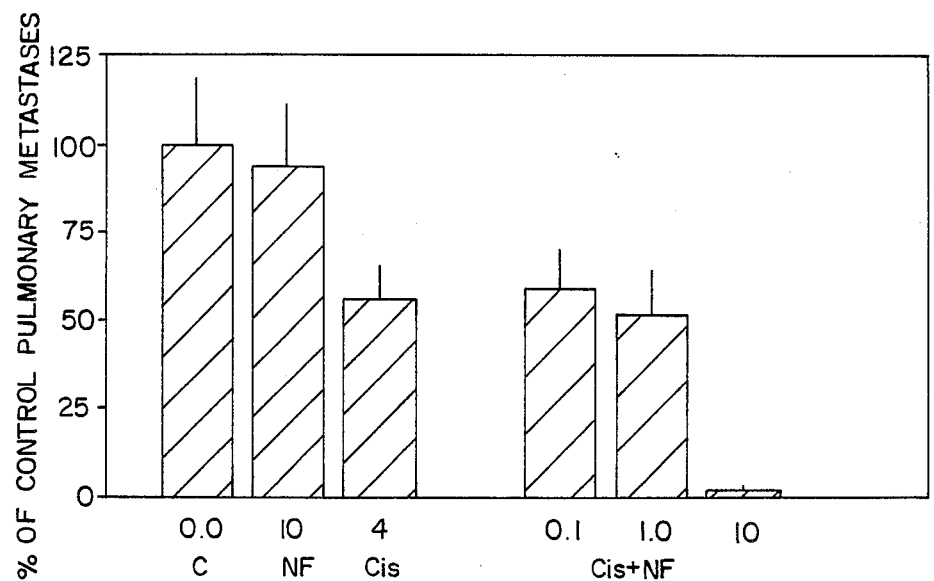
FIG.6a
FIG.6b
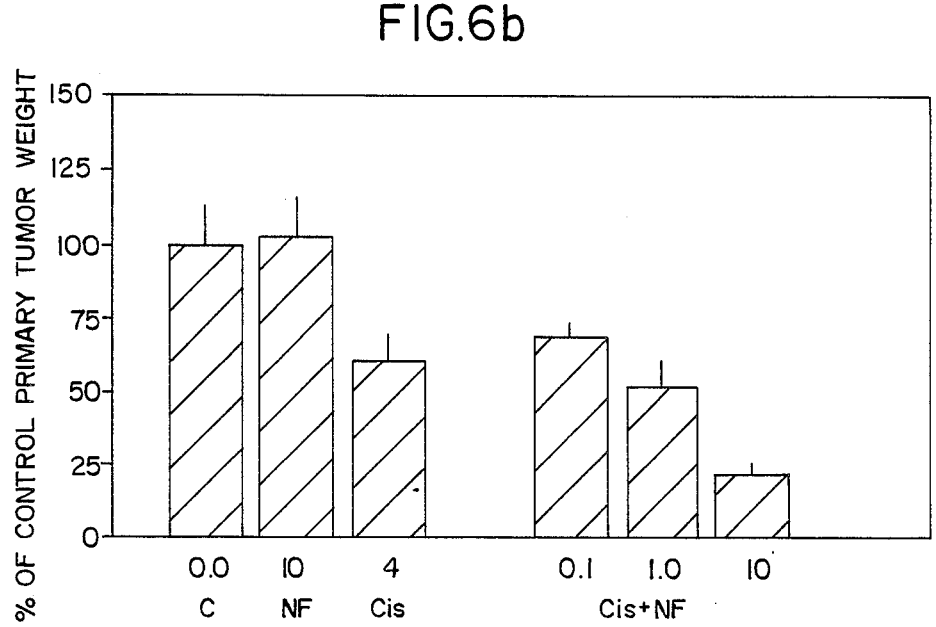

METHOD AND COMPOSITION FOR THE TREATMENT OF TUMORS BY ADMINISTERING A PLATINUM COORDINATION COMPOUND AND A CALCIUM CHANNEL BLOCKER COMPOUND OF THE DIHYDROPYRIDINE CLASS

CROSS-REFERENCE TO RELATED APPLICATION

The present invention is a continuation-in-part of application Ser. No. 480,704, filed Mar. 31, 1983 now U.S. Pat. No. 4,690,935 which has inventors in common with this application and is assigned to a common assignee.

BACKGROUND OF THE INVENTION (1) Field of the Invention

The present invention relates to a method and compositions for the treatment of malignant tumors or metastasis of malignant tumors by administering a platinum coordination compound and a calcium channel blocker compound of the dihydropyridine class. In particular the present invention relates to a method which comprises administering cis-diamminedichloroplatinum (II) and nifedipine, respectively, as the compounds.

(2) Prior Art

Cis-diamminedichloroplatinum (CDDP, cisplatin) is the first inorganic antitumor agent used for clinical cancer therapy. Developed and first described by Rosenberg et al (Nature 205:698, (1965); Nature 222:385, (1969)), cisplatin has proven to be an effective antineoplastic agent not only against germinnal neoplasms as it was first utilized (Einhorn et al., Int. Med. 87:293, 1977) but also against bladder and ovarian cancer and cancer of the head and neck. It is possible that cisplatin alone or cisplatin in combination with other antineoplastic drugs (e.g, adriamycin, vincristine, etc.) may become the accepted standard agent for the chemotherapeutic treatment of a majority of malignancies including those which are usually considered non-responsive to chemotherapy, such as estrogen resistant prostate carcinoma (Merrin, C. E., Cancer Treat. Rep. 63:1579, 1979). This and other platinum coordination compounds are shown in U.S. Pat. Nos. 4,140,707, 4,177,263 and 4,419,351 for instance.

Unfortunately, the development of cisplatin resistance in malignant tumors which initially responded to cisplatin is an all too often encountered problem (Lee et al., Cancer Treat. Rev. 10:39, 1983). As with other chemotherapeutic drugs, cisplatin resistance of the primary tumor and recurrent metastases prevents cisplatin chemotherapy from achieving partial or complete remission rates of more than 15% to 70% for testicular cancer (Stoter et al, Cancer 54:1521, 1984), and ovarian cancer (Belinson et al., Cancer 54:1983, 1984), and 30–40% for cancer of the head and neck (Wittes et al., Cancer Treat. Rep. 63:1533, 1979).

The most serious problem encountered in the chemotherapeutic treatment of cancer is the presence and/or the development of drug resistance by cells of the primary tumor. If the patient dies of metastatic cancer, the cells of the metastatic foci are usually also characterized by their extreme resistance to single or combinations of the available chemotherapeutic drugs. In general, drug resistant tumor cells simply accumulate less (a sublethal dose) of the chemotherapeutic drug(s) than do cells which succumb to the therapeutic agent. Drug resistant tumors can be classified as temporary or permanent (DeVita, V. T., Cancer 51:1209, 1983). Temporary drug resistant tumors are thought to be resistant as a result of physiological factors such as sublethal exposure to drug by tumor cells distant from circulation (i.e., perfusion barrier; Sutherland, R. M., et al., J. Nat. Cancer Inst. 46:113, 1971; and West, G. W., et al., Cancer Res. 40:3665, 1980). Additionally, it has been suggested that the overall growth kinetics of the tumor (Shackney, S.E., et al., Ann. Int. Med. 89:107, 1978) are an important factor in temporary tumor cell resistance (i.e., slowly or asynchronously growing tumor cells would be less likely to be exposed to (accumulate) bolus injected anticancer agents). Permanent drug resistant tumor cells are thought to arise spontaneously, and their probability of existence may be related to tumor mass and/or age. The concept of the spontaneous genetic orgin of drug resistant neoplasms (Goldie and Coldman, Cancer Res. 44:3643, 1984) and tumor heterogeneity in terms of metastatic potential (Fidler, I. J., Cancer Res. 38:2651, 1978) and drug sensitivity (Tanigawa, N, et al., Cancer Res. 44:2309, 1984), has gained widespread acceptance as the mechanism of permanent tumor cell resistance. The two principal mechanisms of permanent drug resistance have been found to be mediated by changes in the concentration or activity of an enzyme in the resistant cells that "inactivates" the drug (Bakka, A., et al., Toxicol. Applied Pharmacol. 61:215, 1981) or by changes in the plasma membrane of the resistant cells which decreases cellular accumulation of drug by inhibiting drug influx and/or by increasing the rate of drug efflux (Giavazzi, R, et al., Cancer Res. 43:2216, 1983; Yanovich, S., et al., Cancer Res. 44:1743, 1984).

Initial attempts to circumvent drug resistance centered on alterations in the scheduling, dosages, and/or method of application of a single chemotherapeutic agent (Benz, C., et al., Cancer Res. 42:2081, 1982; Ozols, R. F., et al., Cancer Res. 42:4265, 1982). Much more promising, however, appears to be combined drug therapy using cytotoxic agents with different mechanisms of action. This type of therapy has improved the cure rate for some cancers but the ultimate failure of even this strategy is well documented (Ling, V., et al., Cancer Treat. Rep. 67:869, 1983; Citrin, D. L., et al., Cancer 50:201, 1982).

Recently, a new methodology has been suggested which may be of great benefit in the chemotherapeutic treatment of cancer. This methodology is centered on the use of agents which function to enhance the initial kill-rate of a cytotoxic drug and/or which enhance the ability of the drug to overcome drug resistant tumors.

Inaba, M., et al., Cancer Res. 39:2200, 1979 reported that the significantly decreased uptake and retention of adriamycin and daunorubicin by P388 leukemia cells resistant to these agents was mediated by an active outward transport of the two cytotoxic agents by resistant cells. These findings suggested that membrane active compounds might be utilized to overcome the outward transport of cytotoxic agents from resistant tumor cells. Riehm and Biedler (1972) reported that they were able to overcome actinomycin D resistance in Chinese hamster cells by treatment with the detergent Tween 80. Subsequently, Valeriote et al (V-aleriote F., et al., Cancer Res. 39:2041, 1979) reported that the membrane active antibiotic amphotericin B was able to enhance the effects of adriamycin and vincristine against AKR leukemia. Tsuruo et al (Cancer Res. 41:1967, 1981) introduced the use of a calcium channel blocker of the phenylakylamine class (verapamil) to overcome vincristine resistance in P388 leukemia in vitro and in vivo. Tsuruo's subsequent reports (Cancer Res; 42:4730; 43:2267 and 44:4303, 1982, 1983c, 1984, respectively) and those of other investigators have clearly established the utility of verapamil (Slater et al, J. Clin. Invest. 70:1131, 1982) and other calcium regulatory compounds (Ganapathi et al, Cancer Res. 44:5056, 1984) as enhancing the cytotoxic effect of these anticancer agents against drug resistant tumors.

It has been demonstrated that verapamil is able to decrease the efflux of adrimycin, vincristine and daunorubicin from untreated and resistant tumor cells. This results in an increased effective intracellular accumulation of the cytotoxic agent and results in a decrease in the LD50 concentration of the antitumor agent. The ability of daunorubicin resistant and sensitive Ehrlich ascites carcinoma cells to accumulate and retain daunorubicin is inversely related to the concentration of $Ca^{2+}$ in the incubation medium (Murray et al, Cancer Chemotherap. Pharmacol. 13:69, 1984). Verapamil's ability to increase daunorubicin cytotoxicity in resistant Ehrlich tumor cells may be at least partially attributable to its (verapamil) abiltty to inhibit calcium influx, which would have effects similar to those obtained by decreasing extracellular $Ca^{2+}$.

The cytotoxic mechanism of action of cisplatin is known to be its ability of the platinum moiety to form DNA-DNA and DNA-protein crosslinks in the target cell nucleus, thus preventing new mRNA transcription and DNA replication (Roberts, J. J., In: Molecular Actions and Targets for Cancer Chemotherapeutic Agents, Academic Press, New York, p. 17, 1981). The exact mechanism of resistance to cisplatin, however, is not known (Curt et al, Cancer Treat. Rep. 68:87, 1984). Sigdestad et al (Cancer Treat. Rep. 65:845, 1981) reported that all phases of the cell cycle (G1, S, G2 and M) of a murine fibrosarcoma were sensitive (in vivo) to cisplatin although cells in the G1 phase were the most sensitive by a factor of 10. This data suggests that slowly growing cells or asynchronously growing tumor cells might be the population of cells that eventually demonstrate cisplatin resistance. Whether the growth rate or phase of cell cycle affects enzyme activity or the membrane of resistant cells (as the basis for cisplatin resistance) is not known.

Because of this lack of understanding of the mechanism of cisplatin resistance, attempts have been made to bypass the problem of cisplatin resistant tumor cells by the development of cisplatin analogs, which are now in clinical trials. Unfortunately, many of the analogs are no more tumoricidal than cisplatin and thus the possibility of resistant tumor populations surviving drug treatment and thus proliferating still remain (Rose et al., Cancer Treat. Rep. 66:135, 1982).

Few investigators have examined the ability of nonchemotherapeutic agents to enhance the antineoplastic effects of cisplatin, perhaps because the mechanism of cisplatin resistance remains unknown. Misonidazole, a radiation sensitizer, was found to enhance the cytotoxic effect of cyclophosphamide and L-phenylalanine mustard but not cisplatin, when tested against the murine reticulum cell carcinoma M5076 (Clement et al, Cancer Res. 40:4165, 1980). In an earlier study using cultured HeLa cells and mouse FM3A cells, verapamil enhanced the cytotoxic effect of peplomycin (a member of the bleomycin group of antibiotics) but failed to enhance the cytotoxic effects of cisplatin (Mizuno and Ishida, Biochem. Biophys. Res. Commun. 107:1021, 1982).

Tsuruo et al (Cancer Res. 41:1967;(1981)) demonstrated in vitro that the calcium channel blocker verapamil enhanced antitumor drug effects against normal and drug resistant murine tumors (Tsuruo et al, Cancer Res. 2:4730, 1982). This enhancement of antitumor drug effect by verapamil appears to be relatively non-specific in that verapamil enhances both vinca alkyloid (Tsuruo et al, Cancer Res. 43:808, 1983a) and anthracycline antibiotic (Tsuruo et al, Cancer Res. 43:2905, 1983b) cytotoxic effects. The ability of verapamil to enhance cytotoxic drug effects is not limited to murine tumor cell lines. Rogan et al (Science 224:994,(1984)(1981) has demonstrated that verapamil overcomes adriamycin resistance against a cultured human ovarian tumor cell line and Tsuruo et al (Cancer Res. 43:2267,(1983c)) reported that verapamil potentiated vincristine and adriamycin effects against human hemopoietic tumor cell lines.

Few investigators have addressed the question of enhancement of antitumor drug effects by calcium channel blockers (CCB) or other membrane active compounds in vivo against normal or drug resistant tumor cell lines. Tsuruo et al (Cancer Res. 41:1967, 1981 and Cancer Res. 43:2905, 1983b) has reported that vincristine and adriamycin resistance in P388 leukeumia can be overcome by verapamil in vivo. Unfortunately the P388 leukemia is an ascites tumor, not a solid tumor, and in humans the majority of fatal malignancies are solid tumors and/or their metastases. Akagawa, S., et al, Kagaku Nyoko 11 943–7 (1984) describe using nicardipine with vindesine sulfate and dichloroplatinum II in the treatment of drug resistant esphageal carcinomas in humans. A partial response was achieved. Akazawa, S. et al found that large dosages (500 nanograms per ml in the blood stream) appeared to enhance the effects of vindesine sulfate (VDS) and diamine dichloroplatinum (II) (CDDP) in treating an esophageal carcinoma. There appeared to be regression of various tumors as a result of the treatment; however, the effective dosage of the nicardipine was large and lower dosages were uneffective. The purpose of the experiment was to enhance the effect of the VDS and not the CDDP.

It has been found, as disclosed in Ser. No. 80,704, that CCB of the dihydropyridine class are more potent in their antimetastatic effects than verapamil. Kessel and Wilberding (Biochem. Pharmacol. 33:1157, 1984) found that verapamil and nitrendipine (a dihydropyridine class CCB) exhibited different modes of action in mediating accumulation of daunorubicin in P388 and P388/ADR resistant cells in culture. Verapamil showed superior ability to enhance the accumulation of daunorubicin in normal cells as compared to resistant cells. In contrast, nitrendipine enhancement of daunorubicin accumulation was identical in both P388 cell lines. Additionally, nitrendipine's ability to enhance the accumulation of daunorubicin in both tumor cell lines was greatly superior (in micromoles) to that of verapamil. Thus independent investigators support the previous published work of Honn et al that the calcium channel blocker compounds of the dihydropyridine class are superior anticancer properties to verapamil. However, there has been no suggestion in the prior art that low dosages of selected calcium channel blockers can be used with a platinum coordination compound for the reduction of metastasis or for the regression of tumors.

OBJECTS

It is therefore an object of the present invention to provide a method and composition for treating malignant tumors or metastasis of malignant tumors which produces regression of the tumor or reduces metastasis. It is preferred to provide an improved method of administering a calcium channel blocker compound of the dihydropyridines class with the platinum coordination compound. Further still it is an object of the present invention to provide a method which is simple and effective. These and other objects will become increasingly apparent by reference to the following description and the drawings.

IN THE DRAWINGS

FIG. 1 is a graph which demonstrates the cytostatic effect of cisplatin against tertiary cultures of B16a tumor cells. The cells labeled CPR-0.25 and CPR-5.0 were primary cultures of B16a cells that were passaged twice in flasks. During each passage, they were treated once daily with cisplatin (CIS) at 0.25 or 5.0 microM, respectively, for four days. On the fifth day the cells were replated. "Normal" cells were passaged twice and treated with saline as controls. The CPR-5.0 cells are significantly resistant to the antiproliferative effects of cisplatin when compared to the "normal" cells and those treated with low (0.25 microM) cisplatin. Each bar represents groups of five flasks (mean+/−SEM).

Figure 2:
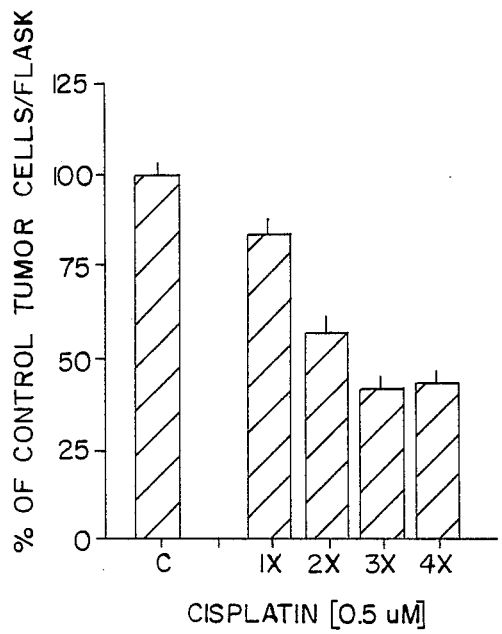

FIG. 2 is a graph which demonstrates the time course for cisplatin inhibition of B16a proliferation. Secondary cultures of B16a cells were plated on day 1 (at 40,000 cells/flask). On day 4 cisplatin was added (0.5 microM/flask). On day 5, the flask labeled 1X was terminated. Media was discarded and adhering cells were removed with trypsin. Cisplatin was added to the remaining flasks, with one group terminated each successive day. The viability of cells for all groups (upon termination) was >85%. The control flasks contained an average of $1.3 \times 10/6$ cells/flask and were set equal to 100% in the graph. The bars represent groups of five flasks (mean +/−SEM).

Figure 3:
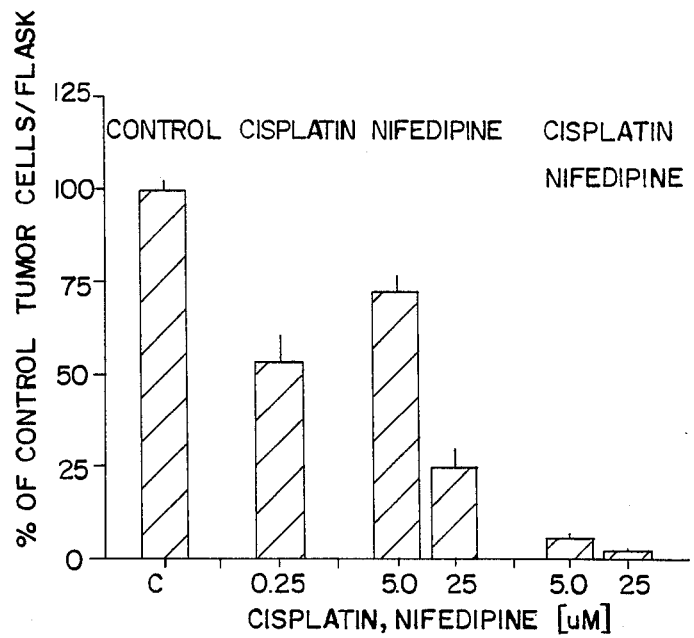

FIG. 3 is a graph which shows the potentiating effects of nifedipine (NF) as the calcium channel blocker compound on the antiproliferative effects of cisplatin in vitro according to the present invention. The inhibitory effects of nifedipine (5.0 microM) and cisplatin added to the same flasks was more than the additive inhibition observed in flasks treated with either drug alone. Cells (40,000/flask) were plated on day 1, drug(s) addition was started on day 4, with daily additions until the day of termination, day 8. Cell viability of adhering cells was >85%. The mean number of cells in the control flask ($1.8 \times 10/6$) was set equal to 100% in the graph. The bars represent groups of five flasks (mean +/−SEM).

Figure 4A:
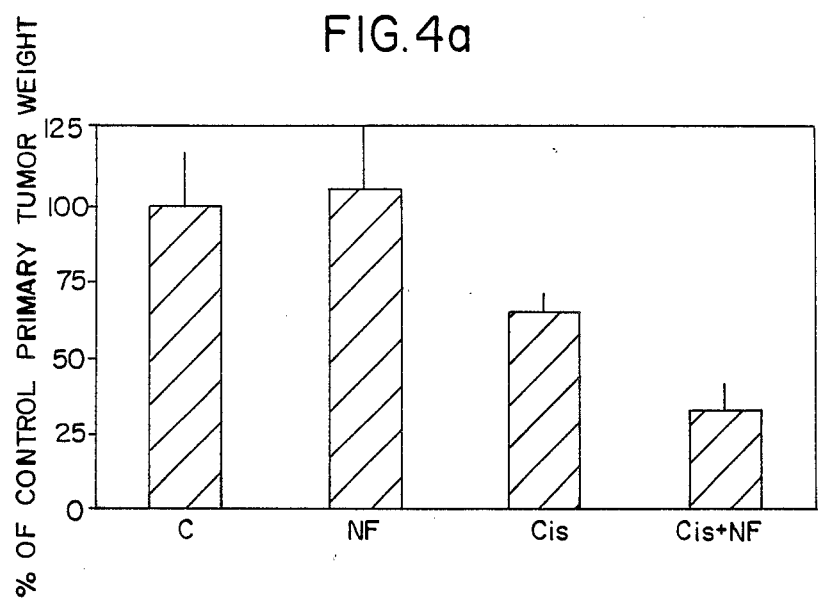
Figure 4B:
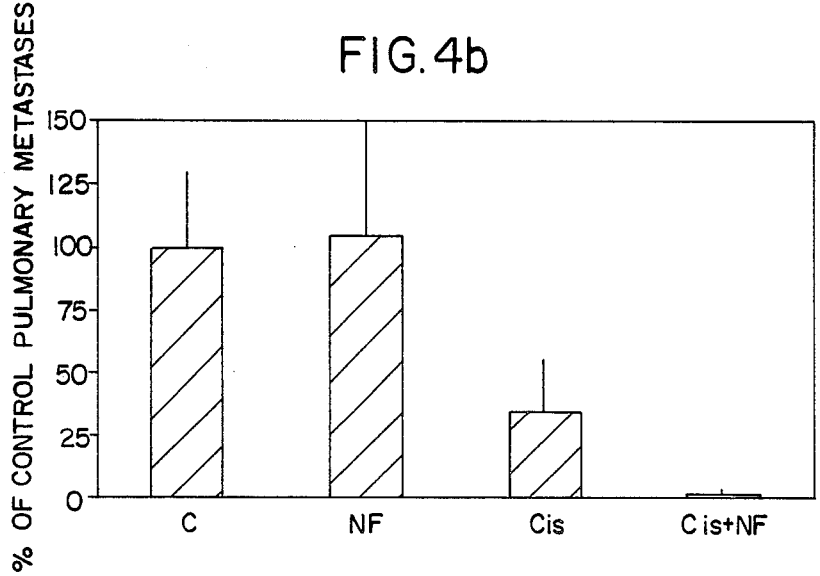

FIGS. 4a and 4b are graphs which present the effects of nifedipine (alone), cisplatin (alone) and nifedipine plus cisplatin on primary B16a tumor weight and number of pulmonary metastases in vivo in mice. Nifedipine (alone) had no significant effect on tumor weight or number of metastases. Cisplatin (alone) significantly ($p<0.05$) decreased both primary tumor weight and the number of metastases. The group treated with nifedipine plus cisplatin had the greatest reductions in primary tumor weight and were completely free of metastases. The bars represent the means +/−SEM for each group, n=5. The means for the control were 29+/−3.5 metastases and primary tumor weight of 2.5+/−0.3 grams.

Figure 5A:
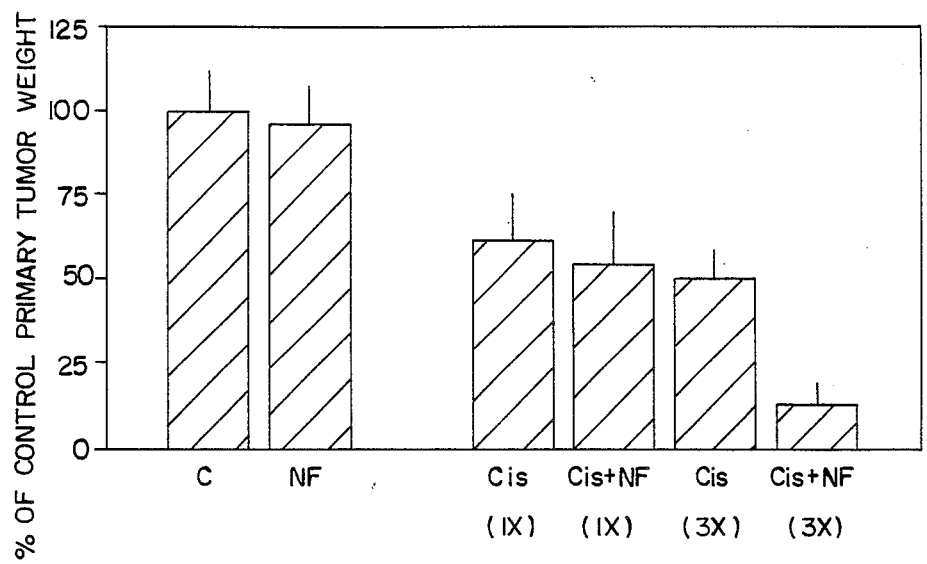
Figure 5B:
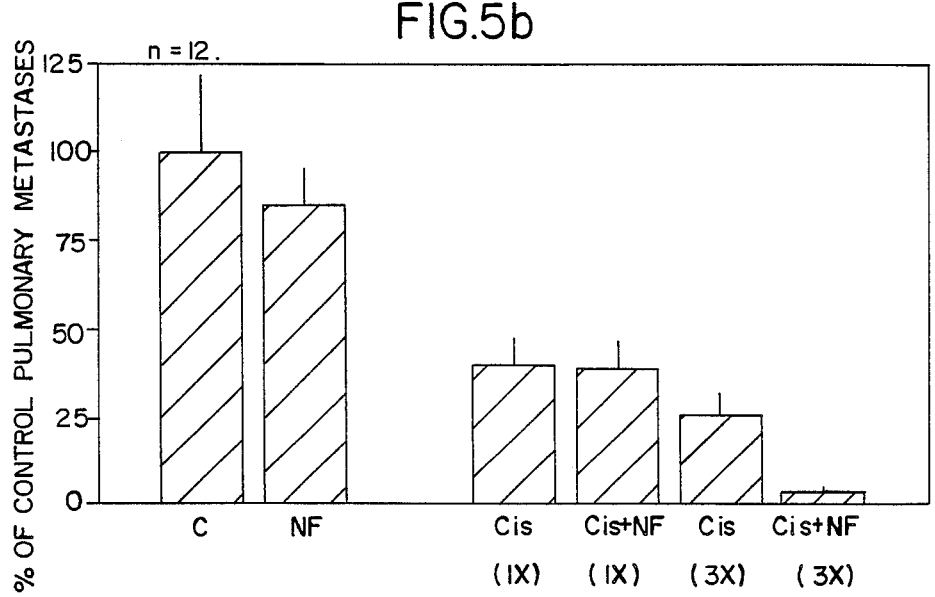

FIGS. 5a and 5b are graphs which depict the effect of nifedipine (alone), cisplatin (alone) and nifedipine plus cisplatin on primary B16a tumor weight and the number of pulmonary metastases in vivo in mice. Treatment with nifedipine (alone) three times ($3\times$) had no effect on either parameter. Treatment with cisplatin (alone) and cisplatin plus nifedipine one time ($1\times$) significantly ($p<0.05$) reduced the primary tumor weight and the number of metastases. There were no differences, however, between the two groups. Three treatments ($3\times$) with cisplatin (alone) and cisplatin plus nifedipine caused further reductions in primary tumor weights and number of pulmonary metastases. The reduction by cisplatin (alone) $3\times$ was not significantly different from $1\times$ cisplatin treatment. The reductions caused by $3\times$ treatment with cisplatin plus nifedipine, however, were significantly ($p<0.01$) reduced not only from the control groups but, also all of the other drug(s) treated groups. The mean number of control metastases was 44+/−5, and primary tumor weight 2.6+/−0.4 gram, n=12.

FIGS. 6 and 6b are graph which show the effects of three administrations of nifedipine (alone), and nifedipine 30 cisplatin on B16a tumor line primary tumor weight and number of pulmonary metastases. Nifedipine (alone, at a dosage of 10 mg/kg body weight) had a significant effect on tumor weight or number of metastases. Cisplatin (alone, at a concentration of 4 mg/kg) caused a significant ($p<0.01$) reduction in primary tumor weight and primary metastases. The groups treated with nifedipine+cisplatin showed a significant ($p<0.001$) antitumor effect, only with the 10 mg/kg nifedipine pretreatment. Nifedipine at the 0.1 or 1.0 mg/kg given prior to ciplatin did not enhance cisplatin's antitumor effects. The bars represent the means +/−SEM of groups of 11 mice.

Figure 7A:
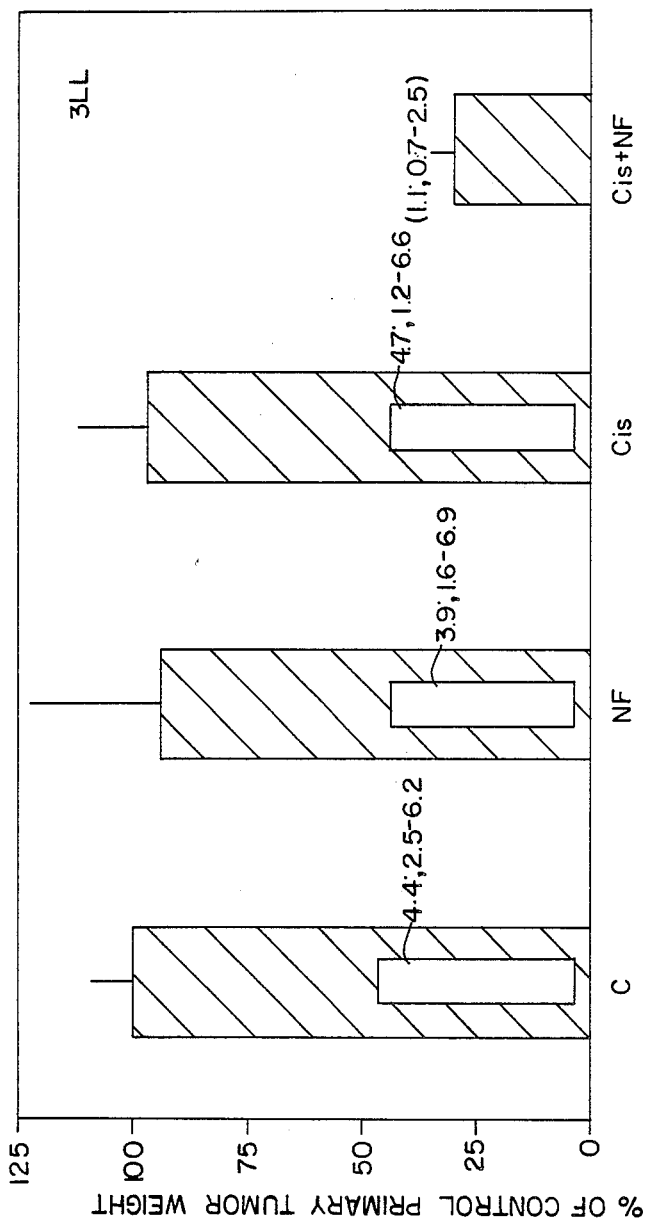
Figure 7B:
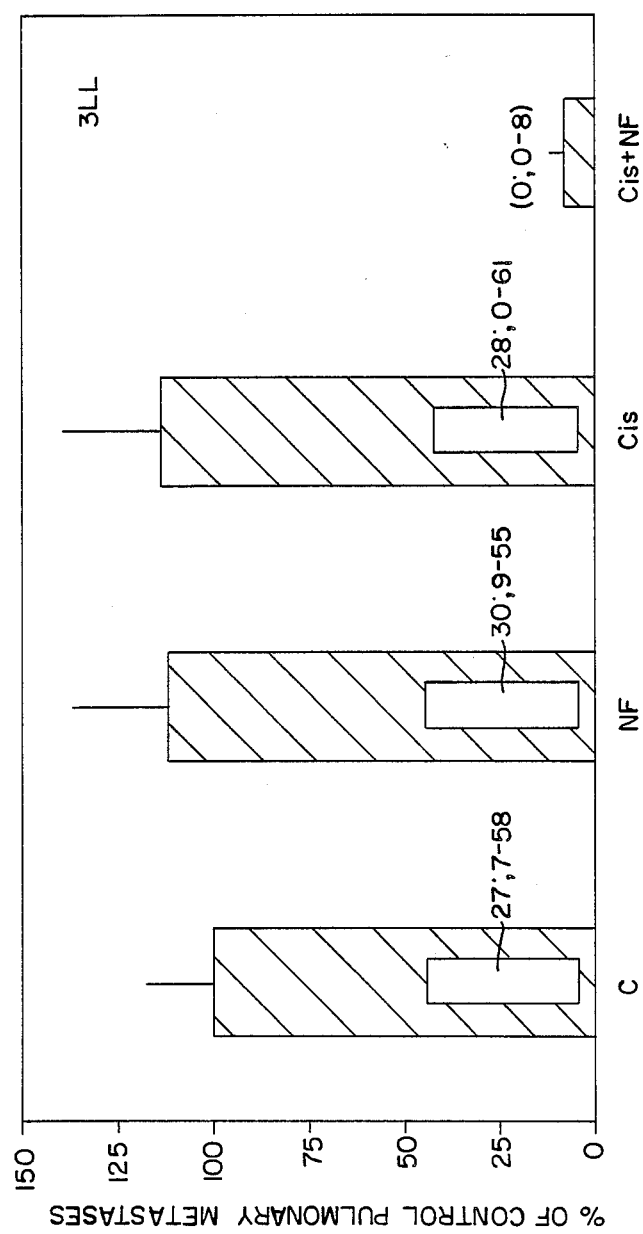

FIGS. 7a and 7b show the effects of two administrations of nifedipine (alone), cisplatin (alone) and nifedipine+cisplatin on Lewis Lung Carcinoa (3LL) primary tumor weight and number of pulmonary metastases. Nifedipine (alone) had no significant effect on tumor weight or number of metastases. Cisplatin (alone) had no significant effect on either tumor weight or the number of metastases. The group treated with nifedipine+cisplatin had significant reductions ($p<0.05$) in primary tumor weight and very significant reductions ($p<0.01$) in number of metastases. The bars represent the means +/−SEM of groups of 11 mice. Mean values for control were 37+/−4.8 metastases and primary tumor weight of 4.3+/−0.4 gm.

Figure 8:
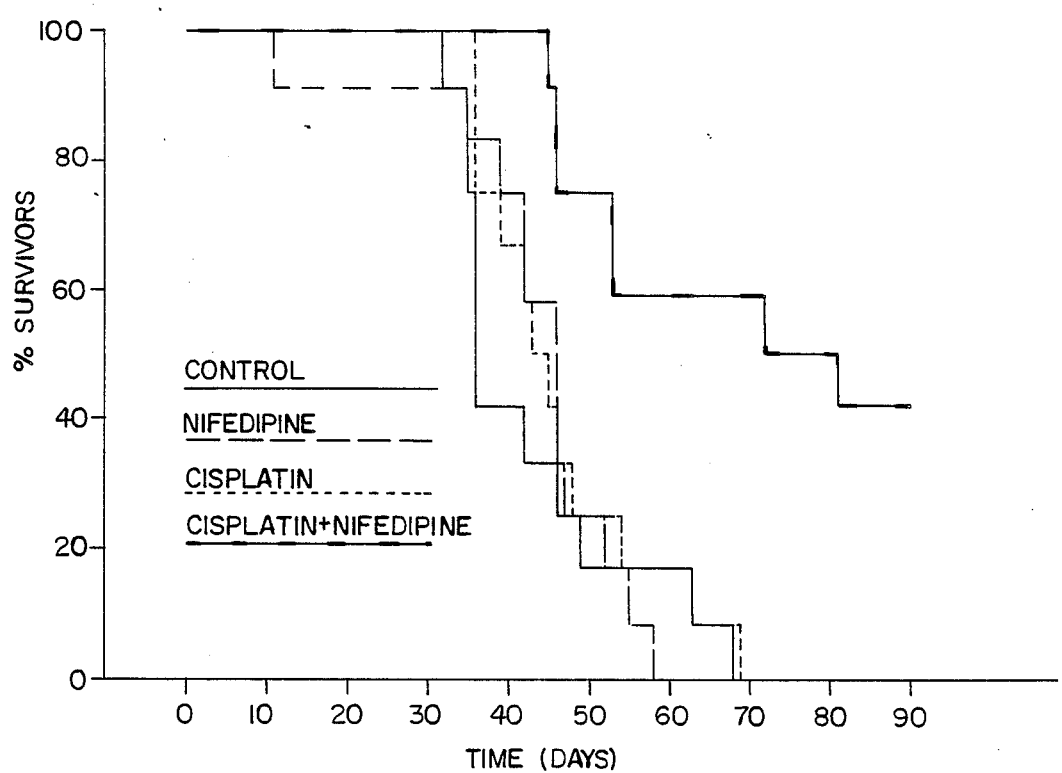

FIG. 8 represents a study comparing the effects of no treatment (control), nifedipine alone (10 mg/kg given orally), cisplatin alone (4 mg/kg given intravenously) and both drugs combined (nifedipine) 20 minutes before cisplatin on mouse survival (in days). Cisplatin resistant B16a cells were taken from culture and injected intravenously (37,000 cells/mouse) on day 0. Drug(s) administered on days 4, 14 and 36. There was approximately a 100% increase in T½ (½ survival time) in the combined drug treated group as compared to the average for the other three drug groups.

GENERAL DESCRIPTION

The present invention relates to a method for the treatment of a malignant tumor in vitro or in vivo in a mammal which comprises: administering to the tumor a calcium channel blocker compound of the dihydropyridine class selected from the group consisting of

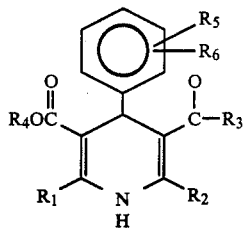

wherein $R_1$ and $R_2$ are methyl groups, $R_3$ and $R_4$ are alkyl or alkyloxyalkylene groups containing 1 to 8 carbon atoms and $R_5$ and $R_6$ are hydrogen or one or two electron withdrawing substituents along with a platinum coordination compound in effective amounts so as to increase regression of the tumor over regression achieved with the platinum coordination compound alone or to reduce metastasis of the tumor or to achieve regression of the tumor and reduction of metastasis.

The present invention further relates to a method for the treatment of a malignant tumor in vivo in a mammal which comprises administering to the tumor a calcium channel blocker compound of the dihydropyridine class selected from the group consisting of

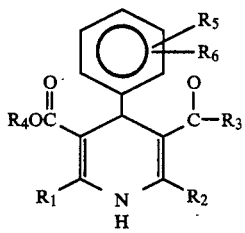

wherein $R_1$ and $R_2$ are methyl groups and $R_3$ and $R_4$ are alkyl or alkyloxyalkylene groups containing 1 to 8 carbon atoms and $R_5$ and $R_6$ are hydrogen or one or two electron withdrawing groups along with a platinum coordination compound in effective amounts and in at least two separate dosages of each compound over a period of days to increase regression of the tumor over the regression achieved with the platinum coordination compound alone or to to reduce metastasis of the tumor or to both achieve regression and reduction of metastasis.

The present invention further relates to a composition for the treatment of malignant tumors in vivo in a mammal which comprises: a calcium channel blocker compound of the dihydropyridine class selected from the group consisting of

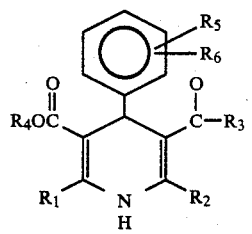

wherein $R_1$ and $R_2$ are methyl groups, $R_3$ and $R_4$ are alkyl or alkyloxyalkylene groups containing 1 to 8 carbon atoms and $R_5$ and $R_6$ are hydrogen or one or two electron withdrawing substituents; and a platinum coordination compound which has antitumor properties in humans wherein the weight ratio of the calcium channel blocker compound to the platinum coordination compound is between 1 and 1000 and 10 to 1.

The compounds can be administered orally in the form of tablets, capsules, or dragees when admixed with solid excipients such as lactose, sucrose, starch, gelatin, microcrystalline cellulose, magnesium stearate or talc. The foregoing compositions are preferred means for oral administration over the use of flavored syrups or tinctures. Parenteral administration can be used employing an aqueous solution, an aqueous ethanol solution or, an oleaginous formulation of the agent. Aqueous solutions can be prepared in water, physiological saline, Ringer's solution, or the like, either with or without buffers. Oleaginous formulations may be made in natural oils (as, peanut oil or olive oil), or in benzyl benzoate, for example. Preferably the calcium channel blocker compound is given orally and the platinum coordination compound is given by injection.

The preferred compounds are nifedipiene, nimodipene, niludipine, nisoldipine, nitrendipine and felodipine. These are all closely related homologs or analogs. Preferably the electron withdrawing group is a nitro or halo group (fluoro, chloro, or bromo) as is known to those skilled in the art.

SPECIFIC DESCRIPTION

Experimental Design and Methods

1. Tumors

The B16 amelanotic melanoma (B16a) and Lewis lung carcinoma (3LL) were selected for the in vivo experiments because they are representative of two histologically distinct tumor types of spontaneous origin, both are spontaneously metastatic to the lung and both are syngeneic to the same mouse strain (C57BL/6J). Additionally, both lines can be dispersed and elutriated (see 2 below) using the same protocol, and both lines can be placed in culture, and injected into mice subcutaneously and via the tail vein. Both tumor cell lines were originally obtained from the DCT Human and Animal Investigation Tumor Bank of the National Cancer Institute , Washington, D.C. The tumors were maintained by passaging in syngeneic (male, 20–22g) C57BL/6J mice (Jackson Laboratories). Tumor metastatic potential is not stable during large numbers (>10) of isotransplants. Therefore, stock tumors were renewed from liquid $N_2$ frozen cells (representing tumors from the first isotransplant generation post receipt from DCT) after every six isotransplants.

2. Separation of Tumor Cells

All of the in vivo studies described by the prior art utilize monodispersed cells obtained from primary subcutaneous tumors. Subcutaneous tumors were dispersed by sequential collagenase digestion as previously described (Sloane, et al., Science, 212, 1151–1153 (1981). Dispersed cells are then purified from contaminating host lymphocytes, macrophages, RBC's, etc, by centrifugal elutriation as previously described by Sloane et al. Elutriated fractions of tumor cells were combined in equal proportions to give a final monodispersed suspension of >3% host cell contamination and >95% tumor cell viability.

4. Cisplatin

Commercially available cisplatin from Bristol Laboratories, Syracuse, New York was used. The compound (cis-diammindichloroplatinum) is available as a white lyophilized powder containing 10 mg mannitol and 9 mg NaCl for each mg of cisplatin. The preparation was suspended in sterile glass distilled water at a concentration of 16 mg/ml which is equivalent to 4 mg/kg cisplatin when injected i.v. at 0.1 ml/mouse.

5. Primary Tumors

Primary subcutaneous tumors were formed by the s.c. injection of 100,000 viable elutriated tumor cells (in 0.1 ml) as previously described (Honn, K. F., et al., Clin. Exp. Metastasis 2:61, 1984).

6. Initial Drug Dosage and Injection Schedule

A cisplatin dose of 4 mg/kg was selected based upon the work published by Chahinian, A. P., et al., Cancer Res. 44:1688, 1984), who reported an acceptable mortality rate of 24% (over 60 days) when this dose of cisplatin (4 mg/kg) was given weekly for 3 weeks tested this dose of cisplatin in C57BL/6J mice and found a mortality rate of 0% over 45 days (in non-tumor bearing mice) The 10 mg/kg dose of nifedipine was selected on the basis of previous work by the inventors herein described in Ser. No. 480,704 on the antimetastatic and antithrombogenic effects of nifedipine (Honn, K. V., et al, Proc. Soc. Expl. Biol. Med. 174:16, 1983); Onoda, , J. M., et al., Thromb. Res. 34:367, 1984). Nifedipine was administered orally 20 minutes prior to the tail vein injection of cisplatin based on human pharmacokinetic studies which indicated that peak plasma levels of nifedipine are achieved approximately 20 minutes post oral administration of drug (in polyethylene glycol 400) and decline in concentration over a one to two hour period (Flaim and Zlis, Fed. Proc. 40:2881, 1981). A maximum host and tumor cell exposure to nifedipine was to be obtained prior to the tail vein injection of cisplatin. Cisplatin accumulates in tumor cells immediately post injection (Bernard, P. P., et al., Cancer Treat. Rep. 67:457, 1983) and may be inactive or cleared from plasma in as little as one hour post administration (Robins, A. B., et al., Cancer Treat. Rep. 67:245, 1983). The days of administration of drugs were selected on the basis of primary tumor cell size, probability of the presence of pulmonary metastases, and tolerance of the mice for cisplatin's side effects (Guarino, A. M., et al., Cancer Res. 39:2204, 1979). In previous studies it was observed by the inventors that pulmonary metastases have developed from primary B16a tumors by day 14 post tumor cell implantation and as early as day 10–14 in the footpad metastasis model. Because the antimetastatic effects of cisplatin as well as its effects against the primary tumor were to be observed, day 14 was chosen as the first day for the injection schedule. The mice were injected on days 17 and 25 (post tumor cell implantation) because they appeared to have recovered and/or stabilized from the previous cisplatin injection as judged by their physical appearance, body weight and activity. Therefore, the drugs (nifedipine and cisplatin) were administered once daily on days 14, 17 and 25 post tumor cell implantation. The studies were terminated on day 33, primarily because the non-drug treated mice were extremely ill from effects of the primary tumor and pulmonary metastases and close to death. Tumor bearing groups of mice were injected with nifedipine alone with subsequent tail vein injection of saline, or were injected with cisplatin alone with prior administration of polyethylene glycol 400 (as drug control groups). Mice were anesthesized with ether and sacrificed by cervical dislocation. The primary tumors were removed and blotted wet weights obtained. The lungs were removed and fixed in Bouin's fixative and macroscopic pulmonary tumors were enumerated.

RESULTS

Nifedipine was chosen to examine in vitro and in vivo for ability to enhance the cytostatic, cytotoxic and antimetastatic effects of cisplatin on the basis of our previous work involving calcium channel blockers as antimetastatic agents as described in U.S. application Ser. No. 480,704, filed Mar. 31, 1983. In addition, nifedipine is in clinical use (for the treatment of cardiovascular disorder).

B16 amelanotic melanoma, a murine tumor cell line was adapted for growth in culture. Proliferation studies were conducted using cells in log phase growth with drug added once daily. FIG. 1 depicts the cytostatic effects of cisplatin against secondary cultures, of B16a cells that were previously untreated with cisplatin (normal), and those treated for two passages with a low (0.25 microM) dose of cisplatin (CPR-0.25) or a higher (5.0 microM) dose of ciisplatin (CPR-5.0). The cytostatic effects of cisplatin were similar against normal B16a cells and those previously treated with a low dose of cisplatin. The cells previous exposed to a higher concentration of cisplatin were resistant to the cytostatic effects of a third expouure to cisplatin. It was observed that the proliferation rate for the normal B16a cells and the CPR-0.25 cells was approximately twice that of the CPR-5.0. The mean number of cells in the control flasks as $9.2 \times 10^5$ cells/flask in the normal group, $8.3 \times 10^5$ cells/flask in the CPR-0.25 (cisplatin sensitive group) and $3.7 \times 10^5$ cells/flask in the CPR-5.0 line (the cisplatin resistant group). These results suggested that cisplatin resistance in cultured B16a tumor cells may be a function of the growth kinetics or cell cycle of the resistant cells. To test this hypothesis, we treated normal B16a cells in log phase growth for 1 to 4 days with daily administration of cisplatin (0.5 microM) and observed that after 2 days of administration, maximum cytostatic effects were achieved (FIG. 2). From these preliminary experiments, we concluded that a cisplatin cytostatic enhancing agent should be examined for effects against normal B16a cells in culture as opposed to cisplatin resistant cells in order to maximize the conditions of cisplatin sensitivity by using rapidly proliferating normal tumor cell populations. The mechanism of resistance for cultured B16a cells may not only be a function of the tumor cell membrane (affecting the intracellular accumulation of cisplatin), but also a function of cell cycle or growth kinetics.

Nifedipine was tested for its ability to enhance the cytostatic/cytotoxic (antiproliferative) effects of cisplatin. It was found that nifedipine enhanced the antiproliferative effects of cisplatin as shown in FIG. 3. It was previously observed by us that daily application of pharmacological dosages of CCB can inhibit the proliferation of B16a tumor cells in culture. Although we observed that nifedipine alone slightly inhibited B16a proliferation, it is apparent that the effects of the nifedipine plus cisplatin are more than additive. Therefore, it was concluded that the enhanced antiproliferative effects of cisplatin induced by nifedipine in vitro were due to the synergistic actions of the two compounds and were not attributable only to their additive effects.

Based upon the in vitro testing it was hypothesized that nifedipine may have the ability to enhance the cytotoxic/cytostatic effect of cisplatin in vivo against subcutaneous B16a primary tumors and against their (pulmonary) metastases. The in vitro data suggested that multiple administrations of cisplatin are necessary for cytostatic effects against B16a cells (FIG. 2). Therefore, the protocol was centered around multiple three times (3×) administrations of nifedipine and cisplatin over a 12 day period. Nifedipine was administered orally to B16a tumor bearing mice 20 minutes prior to the tail vein injection of cisplatin. In humans, peak plasma levels of nifedipine are achieved approximately 20 minutes post oral ingestion (Flaim and Zelis, Fed. Proc. 40:2881, 1981). Having no murine pharmacokinetic data, human kinetic data was used. It was hypothesized that nifedipine could enhance the cytotoxic/cytostatic effects of cisplatin by: (1) increasing the levels of cisplatin in cells of the primary tumor, including those potentially in the hypoxic zone of the tumor (West et al, Cancer Res. 40:3665, 1980) by increasing blood flow to the tumor (Kaelin, W. G., et al., Cancer Res. 42:3944, 1982), or (2) by increasing the maximum intracellular levels of cisplatin by altering tumor cell membrane characteristics related to cisplatin transport/permeability (Yanovich and Preston, Cancer Res. 44:1743, 1984) or (3) by inhibiting $Ca^{2+}$-dependent enzymes needed to repair cisplatin effects on tumor cell DNA (Chafouleas, J. G., et al., Science 224:1346, 1984).

In a preliminary in vivo study (FIGS. 4a and 4b), nifedipine and cisplatin were administered sequentially on days 14, 17 and 23 post tumor cell implantation. Nifedipine alone, had no effect on primary tumor weight or the number of pulmonary metastases. Cisplatin, alone significantly reduced primary tumor weight and the number of metastases, and the group which was administered nifedipine and cisplatin were completely free of pulmonary metastases and had a further reduction in primary tumor weight to the extent that the tumor weight was significantly reduced from the mean tumor weight of the cisplatin group. The second in vivo experiment followed the same basic protocol as the first, but with two additions. The number of mice per group was increased from 5 to 12 and two additional groups were added, cisplatin alone and nifedipine plus cisplatin with both new groups receiving only one administration of drug(s).

As depicted in FIG. 5, a single administration of cisplatin was sufficient to reduce the average tumor weight and number of pulmonary metastases, but nifedipine failed to enhance the effects of cisplatin. The groups receiving three treatments of cisplatin and nifedipine plus cisplatin reproduced the results observed in the preliminary study. There was a significant reduction in mean tumor weight and the number of metastases in the group receiving cisplatin 3× when compared to control or the group which received cisplatin once. The group receiving nifedipine and cisplatin 3× showed a further reductio mean tumor weight and number of pulmonary metastases that was significantly reduced from not only the control group, but also the group treated only with cisplatin 3×.

Using the B16a tumor line, the same time course of drug injection and day of experiment termination was followed as previously. The experimental protocol was varied by increasing the number of groups receiving combined drug therapy from one to three. For these three groups, we held the cisplatin dosage constant (as used above) at 4 mg/kg body weight and varied the nifedipine dosage. One group received 0.1 mg/kg, the second group received 1.0 mg/kg and the third group received 10.0 mg/kg. As depicted in FIG. 6, the ability of nifedipine to enhance cisplatin antitumor effects was positively correlated with the dosage of nifedipine. As the concentration (dosage) of nifedipine is increased from 0.1 to 1.0 to 10 mg/kg, the enhancing effects of cisplatin antitumor and antimetastatic effects were also increased. Specifically, the antitumor effects of cisplatin alone (FIG. 6a) caused a significant ($p<0.01$) reduction in primary tumor weight when compared to the weights of the control tumors. Nifedipine at 0.1 or 1.0 mg/kg given prior to cisplatin failed to enhance cisplatin's antitumor effects. Pretreatment with 10.0 mg/kg nifedipine, however, 30 significantly ($p<0.001$) enhanced cisplatin antitumor effects as compared to treatment with cisplatin alone or with the two lower dosages of nifedipine. Similar effects on pulmonary metastases are depicted in FIG. 6a. The enhancing effects of nifedipine pretreatment as compared to treatment with cisplatin alone were only observed at the 10 mg/kg nifedipine dose. As shown in both 6a and 6b, 10 mg/kg nifedipine alone had no significant effect on primary tumor weight or pulmonary metastases as compared to the appropriate control groups. Based upon these studies, a preferred dosage of nifedipine is between 0.01 to 20 mg/kg of body weight of the mammal with the lower dosages being give intravenously. A preferred dosage of the cisplatin is 0.1 to 5 mg/kg of body weight of the mammal. Preferably the dosage of cisplatin is 0.4 to 4 mg/kg and the nifedipine is 10 to 20 mg/kg of body weight of the mammal orally. Equivalent dosages of the other dihydropyridines can be used.

The ability of nifedipine to enhance the effects of cisplatin against a histologically different murine tumor cell line, the Lewis lung carcinoma (3LL) was examined. Mice, injected s.c., with Lewis lung carcinoma (3LL) cells were treated on day 14 and 17 post tumor cell injection. The study was terminated on day 23 post tumor cell injection because the control mice were suffering respiratory distress (caused by pulmonary metastasis). Thus, the data presented in FIG. 7 represents the effects of two treatments with nifedipine, cisplatin and nifedipine plus cisplatin. Nifedipine alone had no effect on primary tumor weight or pulmonary metastsis. Treatment with cisplatin alone, also had no effect on primary tumor weight or pulmonary metastasis. The group receiving both drugs, however, exhibited a significant reduction in both primary tumor weight and pulmonary metastasis (with 4/11 mice having no metastasis).

FIG. 8 shows the comparative results for cisplatin alone and nifedipine alone and for the combination of the two. The one-half mean survival time is very significantly increased.

These studies clearly demonstrate the ability of the calcium channel blocker nifedipine to significantly enhance the antitumor and antimetastatic action of cisplatin.

It was also found that mixtures of nifedipine and the cisplatin could be mixed and injected together. This method of administration is no preferred. Since both drugs are currently administered to humans it is believed that the combination will be safe and effective in humans.

Other homologs or close analogs of nifedipine will be effective in the treatment method of the present invention.

The cisplatins with the calcium channel blocker compounds can be particulaly used for the treatment of head and neck, ovarian, testicular, bladder, or colon cancers. The cisplatins are also preferably used in combination with 5- flurouracin or other anticancer agents.

It is intended that the foregoing description be only illustrative of the present invention and that the present invention be limited only to the hereinafter appended claims.

We claim:

1. A method for the treatment of a malignant tumor in vitro or in vivo in a mammal which comprises administering to the tumor a calcium channel blocker compound of the dihydropyridine class selected from the group consisting of

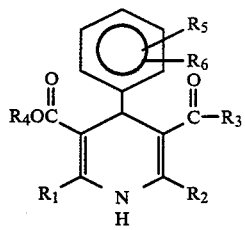

wherein $R_1$ and $R_2$ are methyl groups, $R_3$ and $R_4$ are alkyl or alkyloxyalkylene groups containing 1 to 8 carbon atoms and $R_5$ and $R_6$ are hydrogen or one or two electron withdrawing substituents along with a platinum coordination compound in effective amounts so as to increase regression of the tumor over regression achieved with the plastimum coordination compound alone or to reduce metastasis of the tumor or to achieve regression of the tumor and reduction of metastasis.

2. The method of claim 1 wherein the administrastion is in vivo to the mammal wherein the dosage of the calcium channel block compound is between about 0.01 and 20 mg per kg body weight of the animal and wherein the administration is of the calcium channel blocker compound before the platium coordination compound so that a significant blood plasma level of the calcium channel blocker compound in the mammal is achieved prior to administration of the platinum coordination compound.

3. The method of claim 1 wherein the calcium channel blocker compound is selected from the group consisting of nifedipine, nimodipine, niludipine, nisoldipine, felopipine and nitrendipine.

4. The method of claim 1 wherein the calcium channel blocker compound is nifedipine.

5. The method of claim 1 wherein the platium coordination compound is cis-diamminedichloroplatinum (II).

6. Ammethod for the treatment of a malignant tumor in vivo in a mammal which comprises administering to the tumor a calcium channel blocker compound of the dihydropyridine class selected from the group consisting of

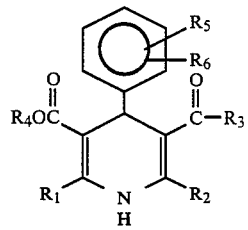

wherein $R_1$ and $R_2$ are methyl groups and $R_3$ and $R_4$ are alkyl or alkyloxyalkylene groups containing 1 to 8 carbon atoms and $R_5$ and $R_6$ are hydrogen or one or two electron withdrawing groups along with a platinum coordination compound in affective amounts and in at least two separate dosages of each compound over a period of days to increase regression of the tumor over the regression achieved with the platinum coordination compound alone or to reduce metastasis of the tumor or to both achieve regression and reduction of metastasis.

7. The method of claim 6 wherein the tumor has not been previously treated with the platinum coordination compound so as to become resistant to regression with the platinum coordination compound alone.

8. The method of claim 6 wherein the administering of each compound consists of three dosages over a period of days.

9. The method of claim 8 wherein each dosage of the platinum coordination compound is between about above 0.1 and 5 mg per kg of body weight of the mammal and the channel blocker compound is between about 0.01 and 20 mg per kg of body weight of the mammal.

10. The method of claim 6 wherein each dosage of the calcium channel blocker compound is between about 10 and 20 mg per kg of body weight of the mammal per day orally.

11. The method of claim 6 wherein the platinum coordination compound is cis-diamminedichloroplatinum (II) and wherein the dosage rate of the platinum complex is between about 0.4 and 4 mg per kg of body weight of the mammal per day over a period of days.

12. The method of claim 6 wherein the mammal is murine.

13. The method of claim 12 wherein the tumor is selected from B-16 amelanotic melanoma and Lewis lung casrcinoma implanted in the murine prior to administering the platinum coordination compound and the calcium channel blocker compound.

14. The method of claim 6 wherein the calcium channel blocker compound is administered to the mammal prior to and after the administration of the platinum ination compound in order to inhibit metastasis of the tumor.

15. A composition for the treatment of malignant tumors in vivo in a mammal which comprises:

(a) a calcium channel blocker compound of the dihydropyridine class selected from the group consisting of

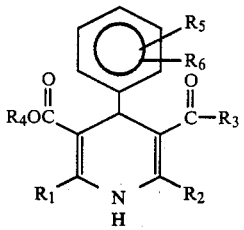

wherein R₁ and R₂ are methyl groups, R₃ and R₄ are alkyl or alkyloxyalkylene groups containing 1 to 8 carbon atoms and R₅ and R₆ are hydrogen or one or two electron withdrawing substituents; and (b) a platinum coordination compound which has antitumor properties in humans wherein the weight ratio of the calcium channel blocker compound to the platinum coordination compound is between 1 and 10 and 10 to 1.

16. The composition of claim 15 wherein the platinum coordination compound is cis-diamminedichloroplatinum (II).

17. The composition of claim 15 wherein the calcium channel blocker compound is nifedipine.

18. The composition of claim 15 wherein the calcium channel blocker compound is nifedipine and the platinum coordination compound is cis-diamminedichloroplatinum (II).

19. The composition of claim 15 in injectable form.

* * * * *

UNITED STATES PATENT AND TRADEMARK OFFICE
CERTIFICATE OF CORRECTION

Page 1 of 3

PATENT NO. : 4,906,646

DATED : March 6, 1990

INVENTOR(S) : Kenneth V. Honn, John D. Taylor and James M. Onoda

It is certified that error appears in the above—identified patent and that said Letters Patent is hereby corrected as shown below:

Column 6, line 24 "graph" should be --graphs--.

Column 6, line 26, "nifedipine 30 cisplatin" should be --nifedipine + cisplatin--.

Column 6, line 36 "ciplatin" should be --cisplatin--.

Column 6, line 41 "Carcinoa" should be --carcinoma--.

Column 7, line 48, "to" (second occurrence), should be deleted.

Column 8, line 23 "nifedipiene" should be --nifedipine--.

Column 9, line 23, after "3 weeks", the following should be inserted --to nude mice. We --.

Column 10, line 27, "ciisplatin" should be --cisplatin--.

Column 10, line 30 "previous" should be --previously--.

Column 10, line 32 "expouure" should be --exposure--.

Column 11, line 61 "reductio" should be --reduction-- and --in-- should be inserted after "reduction".

Column 12, line 18, after "however," "30" should be deleted.

Column 12, line 22, "Fig. 6a" should be --Fig. 6b--.

UNITED STATES PATENT AND TRADEMARK OFFICE
CERTIFICATE OF CORRECTION

PATENT NO. : 4,906,646

DATED : March 6, 1990

INVENTOR(S) : Kenneth V. Honn, John D. Taylor and James M. Onoda

It is certified that error appears in the above—identified patent and that said Letters Patent is hereby corrected as shown below:

Column 12, line 31 "give" should be --given--.

Column 12, line 65, "no" should be --not--.

Column 13, line 40, "plastimum" should be --platinum--.

Column 13, line 43 "administrastion" should be --administration--.

Column 13, line 45 "block" should be --blocker--.

Column 13, line 49 "platium" should be --platinum--.

Column 13, line 52 "platimum" should be --platinum--.

Column 13, line 58 "felopipine" should be --felodipine--.

Column 13, line 61 "platium" should be --platinum--.

Column 13, line 63 "Ammethod" should be --A method--.

Column 14, line 17 "affective" should be --effective--.

Column 14, line 55 "casrcinoma" should be --carcinoma--.

Column 14, lines 60 and 61 "platimum ination" should be --platinum coordination--.

UNITED STATES PATENT AND TRADEMARK OFFICE
CERTIFICATE OF CORRECTION

PATENT NO. :  4,906,646

DATED      :  March 6, 1990

INVENTOR(S) :  Kenneth V. Honn, John D. Taylor and James M. Onoda

It is certified that error appears in the above—identified patent and that said Letters Patent is hereby corrected as shown below:

Page 2, Column 2 under Other Publications, "Bernard, P. P., et at." should be --Bernard, P. P., et al.--.

Column 1, line 33, "germinnal" should be --germinal--.

Column 2, line 64, "(V-aleriote" should be --(Valeriote--.

Column 3, line 2 "phenylakylamine" should be --phenylalkylamine--.

Column 3, line 25, "abiltty" should be --ability--.

Column 4, line 7 "2:4730, 1982)" should be --42:4730, 1982)--.

Column 4, line 35, "esphageal" should be --esophageal--.

Signed and Sealed this

Thirteenth Day of August, 1991

Attest:

HARRY F. MANBECK, JR.

Attesting Officer  Commissioner of Patents and Trademarks